(12) United States Patent
Loveall

(10) Patent No.: US 11,638,804 B2
(45) Date of Patent: May 2, 2023

(54) ELECTRONIC SENSORY SIMULATION SYSTEM

(71) Applicant: Cindy Loveall, Madison, IN (US)

(72) Inventor: Cindy Loveall, Madison, IN (US)

( * ) Notice: Subject to any disclaimer, the term of this patent is extended or adjusted under 35 U.S.C. 154(b) by 707 days.

(21) Appl. No.: 15/863,750

(22) Filed: Jan. 5, 2018

(65) Prior Publication Data

US 2018/0193588 A1    Jul. 12, 2018

Related U.S. Application Data

(60) Provisional application No. 62/443,299, filed on Jan. 6, 2017.

(51) Int. Cl.
*A61M 21/02* (2006.01)
*A61M 21/00* (2006.01)

(52) U.S. Cl.
CPC ....... *A61M 21/02* (2013.01); *A61M 2021/005* (2013.01); *A61M 2021/0016* (2013.01); *A61M 2021/0027* (2013.01)

(58) Field of Classification Search
CPC .......... A61M 21/02; A61M 2021/0016; A61M 2021/0027; A61M 2021/005
See application file for complete search history.

(56) References Cited

U.S. PATENT DOCUMENTS

| 5,253,051 | A | 10/1993 | McManigal | |
|---|---|---|---|---|
| 5,949,522 | A | 9/1999 | Manne | |
| 5,999,105 | A | 12/1999 | Gordon | |
| 2007/0206154 | A1 | 9/2007 | Brady | |
| 2007/0299298 | A1 | 12/2007 | Suissa et al. | |
| 2010/0289973 | A1* | 11/2010 | Jung | A61M 21/00 348/836 |
| 2012/0251989 | A1* | 10/2012 | Wetmore | G09B 19/00 434/236 |

* cited by examiner

*Primary Examiner* — Christine H Matthews
*Assistant Examiner* — Joshua Daryl D Lannu
(74) *Attorney, Agent, or Firm* — Michael C. Balaguy

(57) ABSTRACT

An electronic sensory simulation system including a display screen that simulates visual images or videos with a smell and audio simultaneously. The device effectively includes an electronic sensory simulation system with a docking station that may allow the system to be portable. The electronic sensory simulation system may include a sensory unit assembly which includes a display screen, at least one speaker, at least one scent diffusing mechanism, a user interface, and an input port. The electronic sensory simulation system may further have a docking station so that the sensory unit assembly can be portable or used in a fixed location.

12 Claims, 5 Drawing Sheets

ELECTRONIC SENSORY SIMULATION SYSTEM

CROSS REFERENCE TO RELATED APPLICATION

The present application is related to and claims priority to U.S. Provisional Patent Application No. 62/443,299 filed 2017 Jan. 6, which is incorporated by reference herein in its entirety.

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. FIELD OF THE INVENTION

The present invention relates generally to the field of electronic displays and more specifically relates to sensory simulation with display, smell, and sound.

2. DESCRIPTION OF RELATED ART

The typical activities surrounding modern life often prevent people from being able to spend time in a relaxing environment. Much of the time people are at work or at home so often that these environments become tedious or mundane which in turn can contribute to increasing anxiety and stress. To mitigate the anxiety and stress generated by limited access to more appealing environments, a simulation providing auditory, visual, and olfactory sensory stimulation can be beneficial. However, devices which provide this type of simulation are intended to be statically placed and do not allow the user to easily make use of the beneficial effects in different places. A solution is desired to provide this flexibility.

U.S. Pub. No. 2007/0299298 to David Suissa, et al. relates to a multisensory animated picture. The described multisensory animated picture includes an invention which enables digital works combining fixed images, animated images, sounds and smells to be disseminated to an audience. The multisensory picture looks like a traditional art picture with a removable frame which is personalized in harmony with the work thus disseminated. A high-resolution flat electronic screen (1) occupies the space instead of the picture. Integrated devices enable sounds (2) and smells (3) chosen by the creators of the multisensory works to be disseminated. The invention activates human senses such as sight, hearing, smell and possibly touch, enabling viewers to experience strong emotions.

BRIEF SUMMARY OF THE INVENTION

In view of the foregoing disadvantages inherent in the known electronic displays art, the present disclosure provides a novel electronic sensory simulation system. The general purpose of the present disclosure, which will be described subsequently in greater detail, is to provide a sensory unit assembly that simulates visual images or videos with a smell and audio simultaneously. The present invention is superior to other systems in that it effectively includes an electronic sensory simulation system with a docking station that may allow the system to be portable.

The electronic sensory simulation system may comprise a sensory unit assembly which includes a display screen, at least one speaker, at least one scent diffusing mechanism, a user interface having a plurality of buttons, and an input port. The display screen provides images and/or videos. The images/videos may be scenery selected by a user through the user interface. The user interface includes a plurality of buttons preferably on the side of the sensory unit assembly. The plurality of buttons preferably includes controls for turning the system on/off, a timer, screen dimmer, volume, etc.

The at least one scent diffusing mechanism may stimulate the user's olfactory senses and may diffuse a scent potent enough to permeate the surrounding area. The at least one scent diffusing mechanism may be located within the sensory unit assembly and include an insert for an object that provides the scent. The sensory unit assembly may be removably from the docking station. A charging port may be included in the docking station to provide power to a rechargeable battery located in the sensory unit assembly. A power supply in the form of a removeable cord that plugs into a standard electrical socket may receive power for the charging port. The docking station may hold the sensory unit assembly stationary and in a position desirable for the user to utilize the device. The electronic sensory simulation system may be advantageous for immersion of the following senses: sight, smell, and sound. Simulating these senses may provide the user with the desired sensation and relaxation.

An electronic sensory simulation system is disclosed herein. The electronic sensory simulation system includes a sensory unit assembly, the sensory unit assembly including: a display screen, the display screen may have means of displaying images, video, or animations; at least one speaker, the at least one speaker may have means of playing audio; at least one scent diffusing mechanism, the at least one scent diffusing mechanism may have means of stimulating olfactory senses; a powerer; a user interface, the user interface may have a plurality of buttons for configuring and operating the electronic sensory simulation system, and input ports for receiving information; and a docking station. The docking station includes: a base; the base may have means to allow the electronic sensory simulation system to be removably placed on a horizontal or vertical surface; a docking port; the docking port may have means of temporarily receiving and supporting the sensory unit assembly; a charging interface; the charging interface may have means of nesting within the charging port while the sensory unit assembly may be being supported by the docking port; and a power supply. The power supply may have means of receiving and distributing power to the sensory unit assembly through the charging interface and the charging port.

A method of using the electronic sensory simulation system is also disclosed herein. The method of using electronic sensory simulation system may comprise the steps of: providing an electronic sensory simulation system, the system including: a sensory unit assembly including a display screen, at least one speaker, at least one scent diffusing mechanism, a powerer, a user interface; a docking station including a base, a docking port, a charging interface, and a power supply; docking the sensory unit assembly with the docking station; connecting the power supply with a standard electrical outlet; installing the scent, video, and audio media; activating the electronic sensory simulation system; and configuring desired options.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an electronic sensory simulation system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to electronic displays and more particularly to an electronic sensory simulation system as used to improve sensory simulation with display, smell, and sound.

Generally, the purpose of the invention is to provide calming sounds and video along with the scent that may be associated with the calming sounds and video to allow the user to immerse themselves into a situation that provides relaxation to induce sleep, decrease anxiety, promote healthy meditation and increase well-being.

Figure 1:
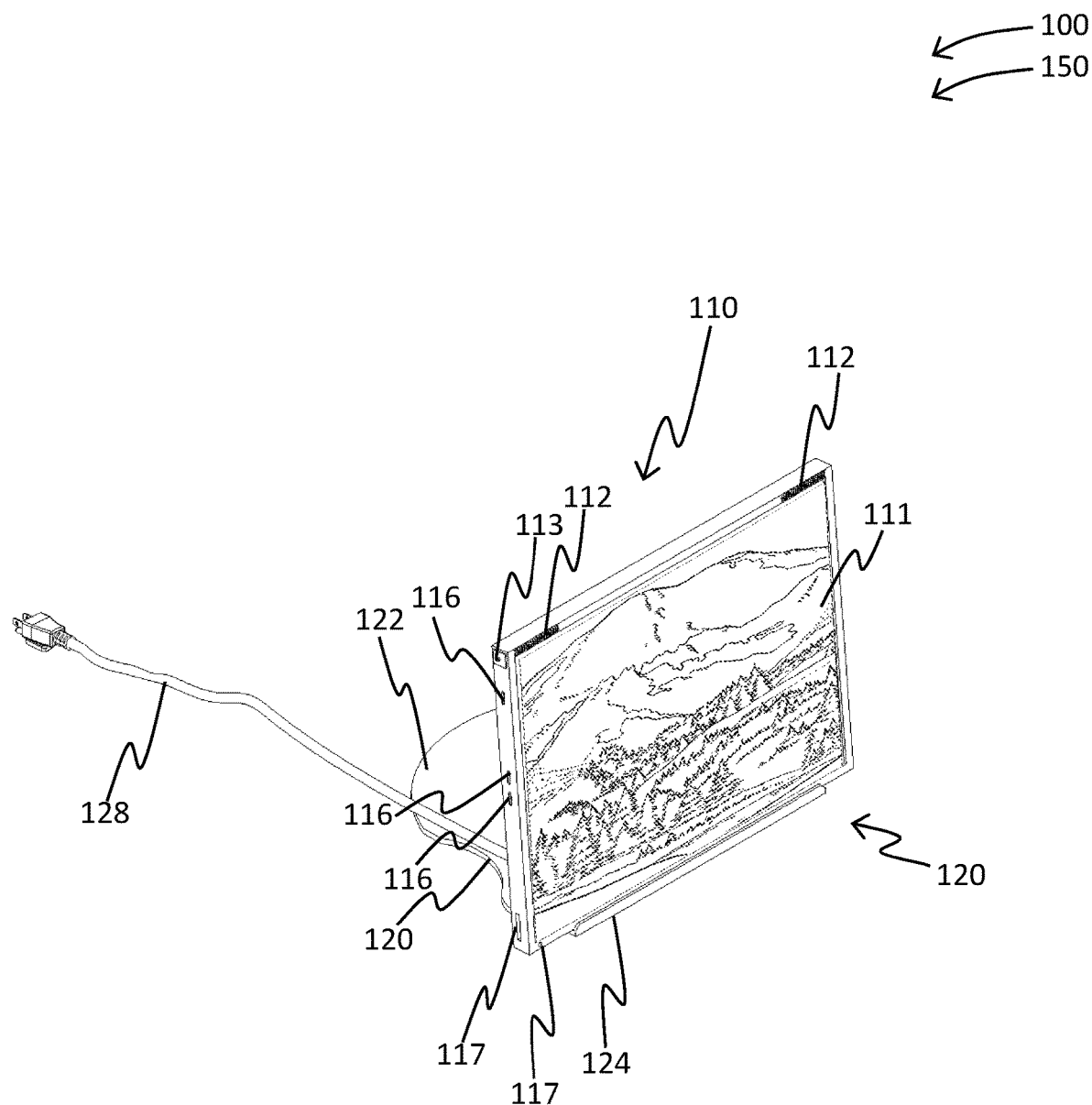
FIG. 1 is a front perspective view of the electronic sensory simulation system during an 'in-use' condition, according to an embodiment of the disclosure.

Referring now more specifically to the drawings by numerals of reference, there is shown in FIGS. 1-4, various views of an electronic sensory simulation system 100. FIG. 1 shows an electronic sensory simulation system 100 during an 'in-use' condition 150, according to an embodiment of the present disclosure.

As illustrated, the electronic sensory simulation system 100 may include a sensory unit assembly 110; the sensory unit assembly 110 including: a display screen 111; the display screen 111 may have means of displaying images, video, or animations; at least one speaker 112. The at least one speaker 112 may have means of playing audio; at least one scent diffusing mechanism 113, the at least one scent diffusing mechanism 113 may have means of stimulating olfactory senses; a powerer 114; a user interface 115. The user interface 115 may have a plurality of buttons 116 used in conjunction with the display screen 111 which provides a graphical user interface that corresponds from input from the user interface 115 for configuring and operating the electronic sensory simulation system 100 to use pre-designed sensory combinations including a pre-defined scent, a pre-defined visual component, and a pre-defined auditory component, such combinations selected from a group consisting of a forest, the ocean, a river, a stream, a waterfall, country scenery, a city, a jungle, snow, rain, a storm, a party, a nightclub, and a restaurant, or to use individual sensory choices selected by the user for scent, visual display, and audio, and also to determine the brightness of the screen, the volume of the audio, and the length of time the electronic sensory simulation system 100 is to be used. Input ports 117 for receiving information via a plurality of sources are selected from the group consisting of an audio in (or auxiliary) jack, SD memory card, microSD memory card, USB, and HDMI; and a docking station 120. The docking station 120 includes: a base 122; the base 122 may have means to allow the electronic sensory simulation system 100 to be removably placed on a horizontal or vertical surface; a docking port 124, (the docking port 124 may have means of temporarily receiving and supporting the sensory unit assembly 110 such that the sensory unit assembly 110 is configured to be portable when not being used with the docking station 120); and a power supply 128. The power supply 128 may have means of receiving and distributing power to the sensory unit assembly 110 through the charging interface 126 on the docking port 124 and the charging port on the sensory unit assembly 110.

Figure 2A:
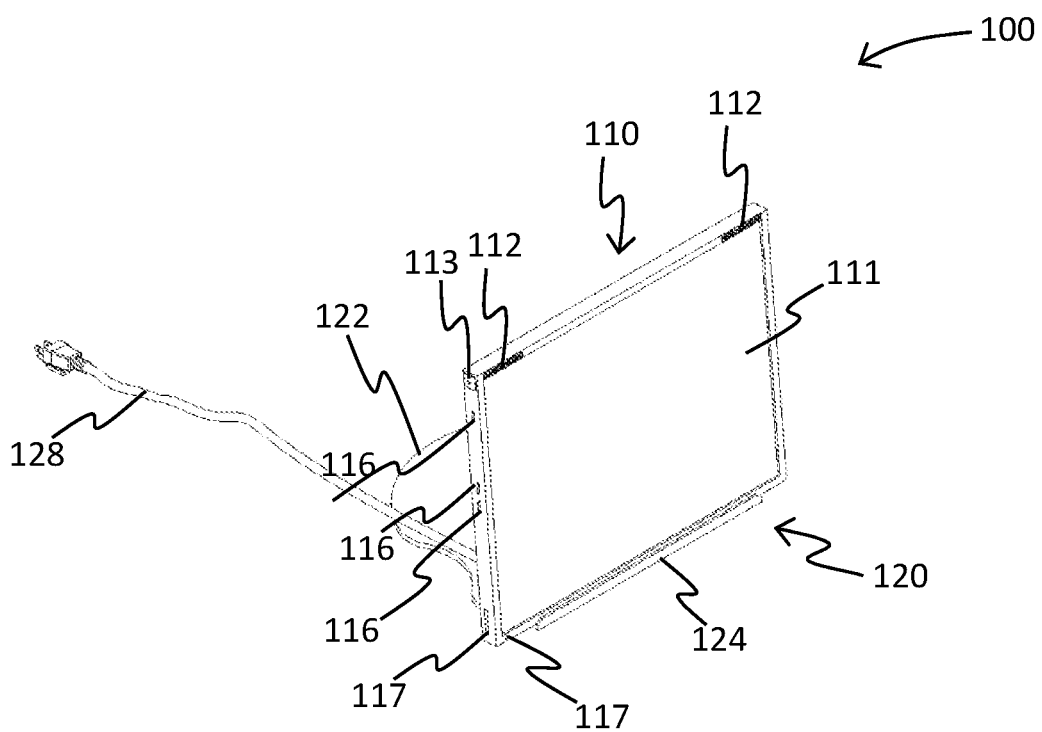
FIG. 2A is a front perspective view of the electronic sensory simulation system of FIG. 1, according to an embodiment of the present disclosure.

FIG. 2A shows a front perspective view of the electronic sensory simulation system 100 of FIG. 1, according to an embodiment of the present disclosure. As above, the electronic sensory simulation system 100 may include a sensory unit assembly 110, the sensory unit assembly 110 including: a display screen 111. The display screen 111 may have means of displaying images, video, or animations; at least one speaker 112. The at least one speaker 112 may have means of playing audio; at least one scent diffusing mechanism 113. The at least one scent diffusing mechanism 113 may have means of stimulating olfactory senses and includes means of replacing or recharging available scents to be diffused which may be provided via mechanisms selected from the group consisting of scent pods, scent cartridges, liquid refill, and essential oils; a powerer 114 which includes a rechargeable battery and charging port; a user interface 115. The user interface 115 may have a plurality of buttons 116 for configuring and operating the electronic sensory simulation system 100, and input ports 117 for receiving information; and a docking station 120; the docking station 120 including: a base 122, (the base 122 may have means to allow the electronic sensory simulation system 100 to be removably placed on a horizontal or vertical surface); a docking port 124, the docking port 124 may have means of temporarily receiving and supporting the sensory unit assembly 110; a charging interface 126, (the charging interface 126 may have means of nesting within the charging port while the sensory unit assembly 110 may be being supported by the docking port 124); and a power supply 128, (the power supply 128 may have means of receiving and distributing power to the sensory unit assembly 110 through the charging interface 126 and the charging port).

Figure 2B:
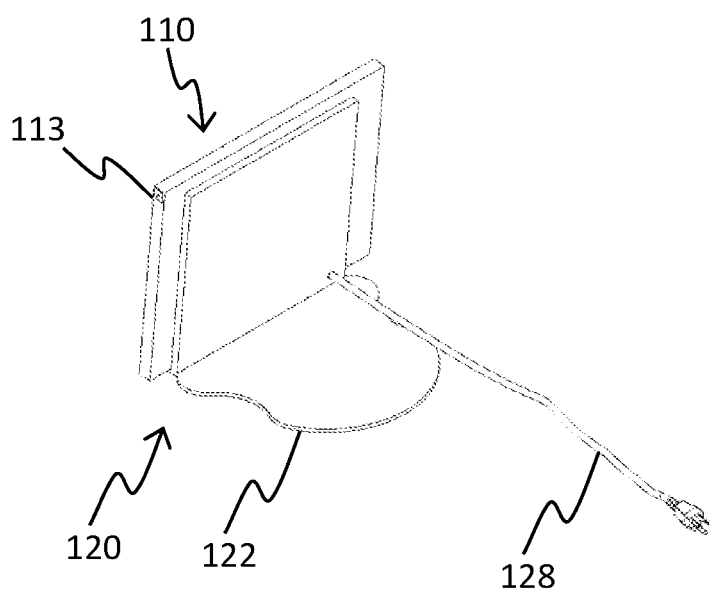
FIG. 2B is a rear perspective view of the electronic sensory simulation system of FIG. 1, according to an embodiment of the present disclosure.

FIG. 2B shows a rear perspective view of the electronic sensory simulation system 100 of FIG. 1, according to an embodiment of the present disclosure. As above, the electronic sensory simulation system 100 may include a sensory unit assembly 110 having at least one scent diffusing mechanism 113; and a docking station 120. The docking station 120 includes: a base 122. The base 122 may have means to allow the electronic sensory simulation system 100 to be removably placed on a horizontal or vertical surface; a docking port 124, the docking port 124 may have means of temporarily receiving and supporting the sensory unit assembly 110; and a power supply 128. The power supply 128 may have means of receiving and distributing power to the sensory unit assembly 110 through the charging interface 126 and the charging port.

Figure 3:
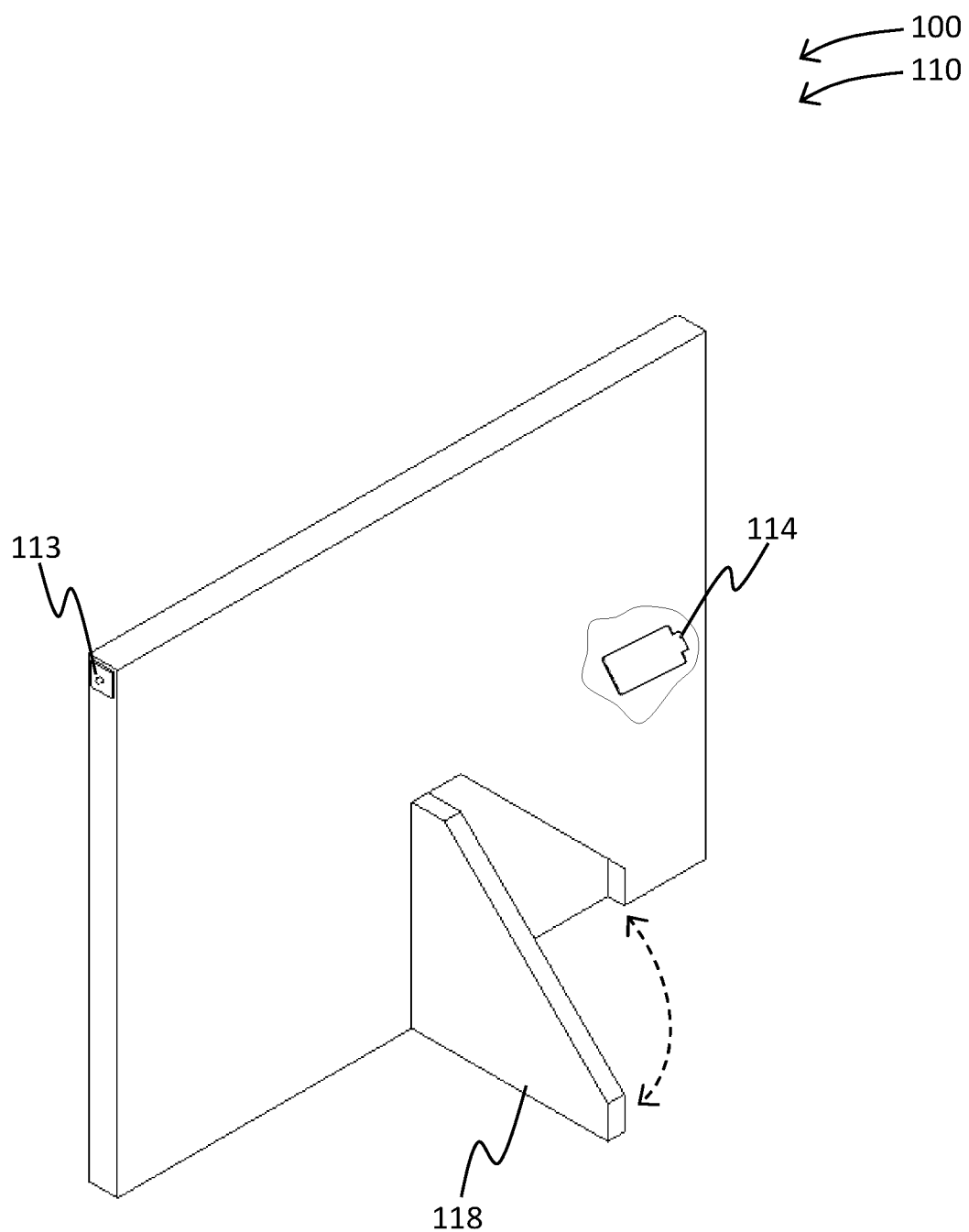
FIG. 3 is a front perspective view of the electronic sensory simulation system of FIG. 1, according to an embodiment of the present disclosure.

FIG. 3 shows a rear perspective view of the sensory unit assembly 110 of FIG. 1, according to an embodiment of the present disclosure. As above, the sensory unit assembly 110 may include at least one scent diffusing mechanism 113; and an extendable support member 118 which allows the sensory unit assembly to be supported in an upright position when on a generally planar horizontal surface and is configured to be stored within the sensory unit assembly 110 during a non-use condition.

Figure 4:
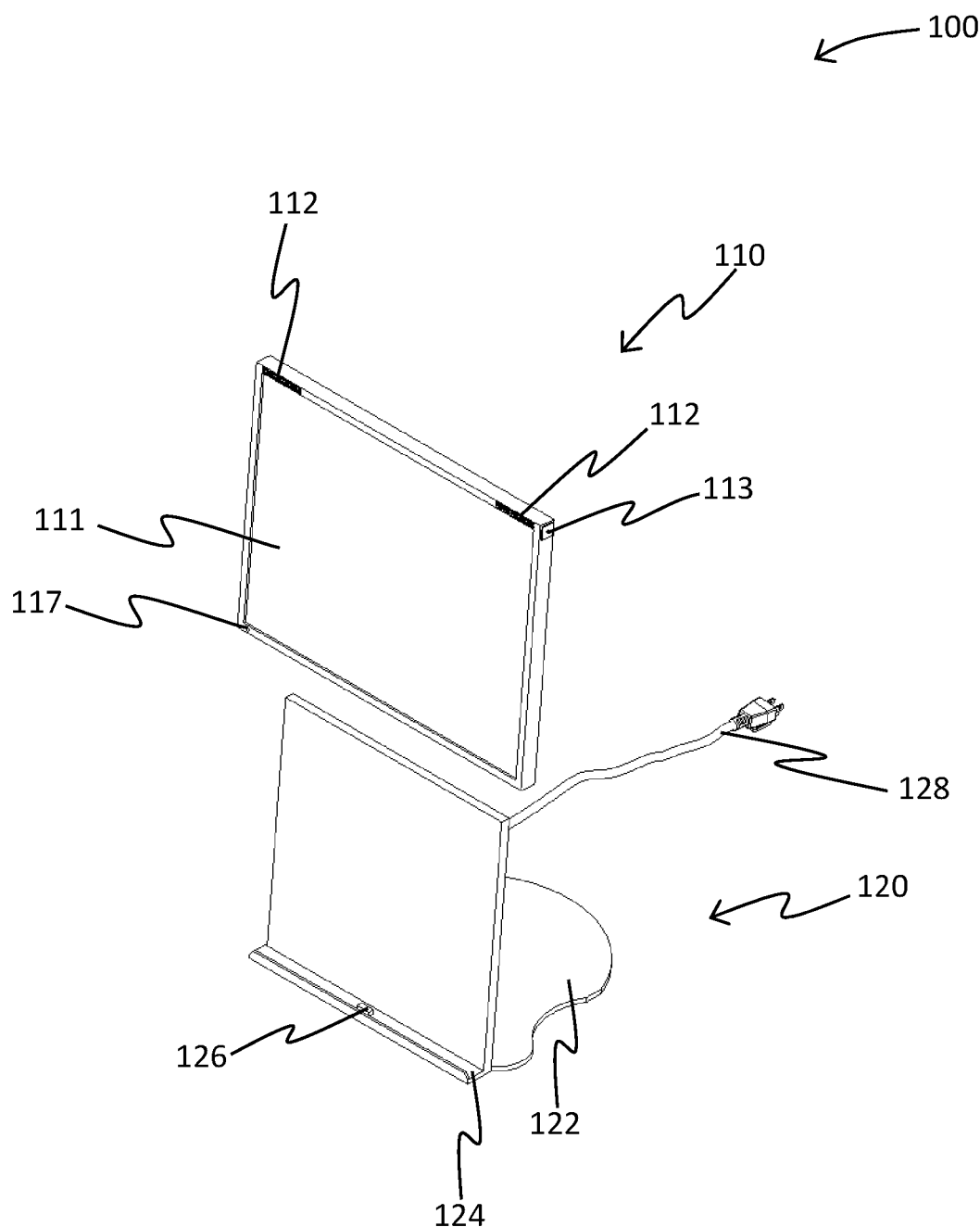
FIG. 4 is a perspective view of the electronic sensory simulation system of FIG. 1, according to an embodiment of the present disclosure.

FIG. 4 shows a front perspective view of the electronic sensory simulation system 100 of FIG. 1, according to an embodiment of the present disclosure. As above, the electronic sensory simulation system 100 may include a sensory unit assembly 110. The sensory unit assembly 110 includes: a display screen 111. The display screen 111 may have means of displaying images, video, or animations; and at least one speaker 112. The at least one speaker 112 may have means of playing audio. The present invention may further comprise at least one scent diffusing mechanism 113; the at least one scent diffusing mechanism 113 may have means of stimulating olfactory senses; a powerer 114; and a user interface 115. The user interface 115 may have a plurality of buttons 116 for configuring and operating the electronic sensory simulation system 100, and input ports 117 for receiving information; and a docking station 120. The docking station 120 includes: a base 122; the base 122 may have means to allow the electronic sensory simulation system 100 to be removably placed on a horizontal or vertical surface; and a docking port 124. The docking port 124 may have means of temporarily receiving and supporting the sensory unit assembly 110. A charging interface 126 may have means of nesting within the charging port while the sensory unit assembly 110 may be being supported by the docking port 124. The present invention further comprises a power supply 128; the power supply 128 may have means of receiving and distributing power to the sensory unit assembly 110 through the charging interface 126 and the charging port.

According to one embodiment, the electronic sensory simulation system 100 may be arranged as a kit. The kit may include a set of instructions; and wherein the system is arranged as a kit. The instructions may detail functional relationships in relation to the structure of the electronic sensory simulation system 100 (such that the electronic sensory simulation system 100 can be used, maintained, or the like, in a preferred manner).

Figure 5:
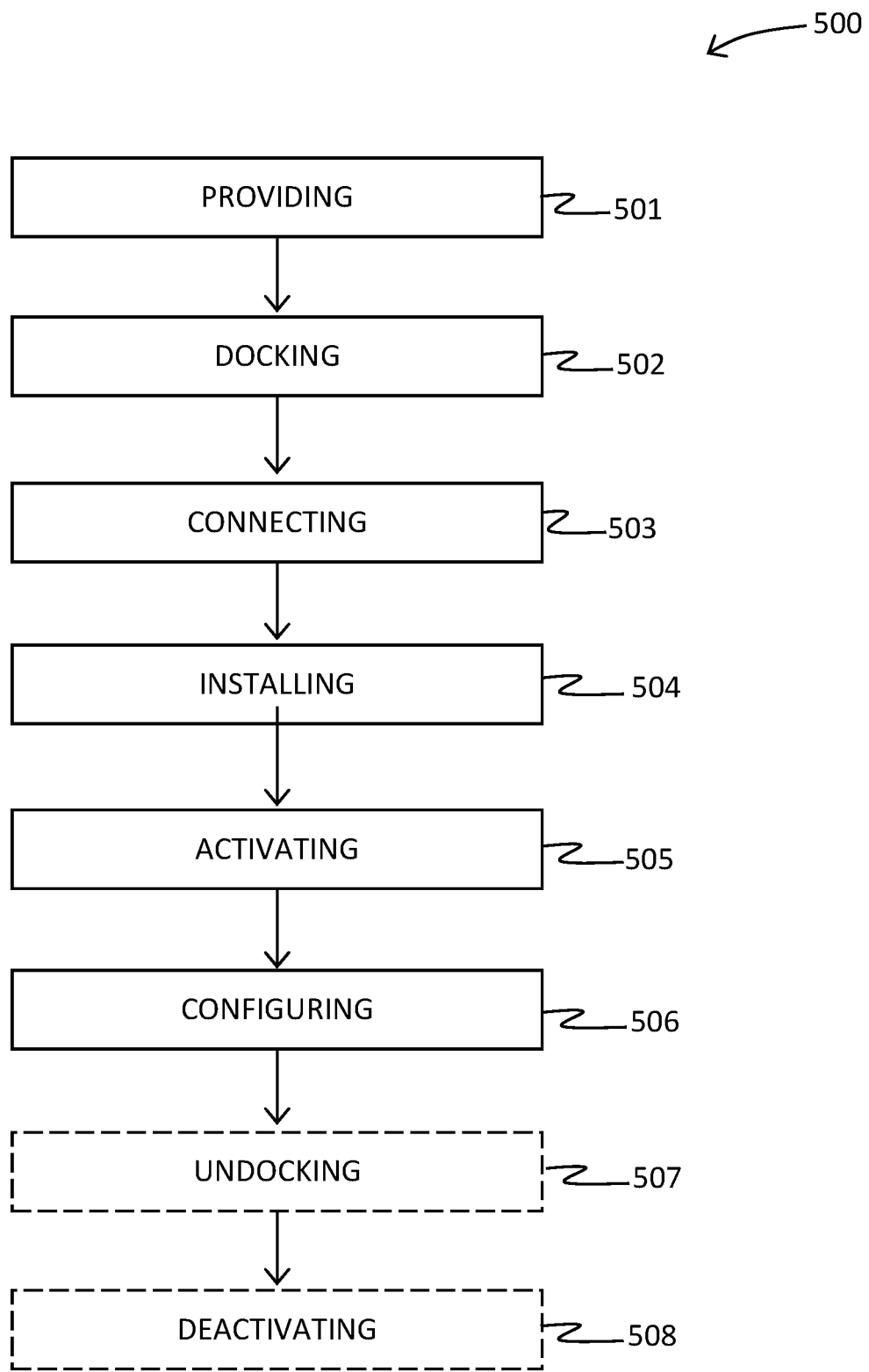
FIG. 5 is a flow diagram illustrating a method of use for electronic sensory simulation system, according to an embodiment of the present disclosure.

FIG. 5 is a flow diagram 550 illustrating a method for using an electronic sensory simulation system, 500, according to an embodiment of the present disclosure. As illustrated, the a method for using an electronic sensory simulation system 500 may include the steps of: providing 501 an electronic sensory simulation system 100, the system including: a sensory unit assembly 110 including a display screen 111, at least one speaker 112, at least one scent diffusing mechanism 113, a powerer 114, a user interface 115; a docking station 120 including a base 122, a docking port 124, a charging interface 126, and a power supply 128; step two 502 docking the sensory unit assembly 110 with the docking station 120; step three 503 connecting the power supply 128 with a standard electrical outlet; step four 504 installing the scent, video, and audio media; step five 505 activating the electronic sensory simulation system 100; and configuring 506 desired options via the user interface 115. The method may further comprise the steps of: undocking 507 the sensory unit assembly 110 from the docking station 120; and deactivating 508 the electronic sensory simulation system 100.

It should be noted that steps 507 and 508 are optional and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for use and installation of the electronic sensory simulation system 100 (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An electronic sensory simulation system comprising:
   a sensory unit assembly, the sensory unit assembly including:
      a display screen for images, video, or animations;
      at least one speaker;
      at least one scent diffusing mechanism having a receptacle configured to receive a scent insert;
      a powerer;
      a user interface, the user interface having a plurality of buttons for configuring and operating the electronic sensory simulation system, and input ports for receiving information; and
   a docking station, the docking station including:
      a horizontal or vertical base;
      a docking port;
      a charging interface between the sensory unit assembly and the docking port; and
      a power supply, wherein
the sensory unit assembly includes an extendable support member which allows the sensory unit assembly to be supported in an upright position when on a generally planar horizontal surface, and
the extendable support member is configured to be stored within the sensory unit assembly during a non-use condition.

2. The electronic sensory simulation system of claim 1, wherein the user interface provides a user with control options to activate or deactivate the electronic sensory simulation system, and make selections for configuring system functions.

3. The electronic sensory simulation system of claim 2, wherein the user interface uses the display screen to provide a graphical user interface which responds to user input from the user interface.

4. The electronic sensory simulation system of claim 3, wherein the sensory unit assembly is capable of being configured with individual sensory choices selected by the user for scent, visual display, and audio.

5. The electronic sensory simulation system of claim 2, wherein the user interface allows the user to determine a brightness of the display screen.

6. The electronic sensory simulation system of claim 2, wherein the user interface allows the user to determine a volume of audio played via the at least one speaker.

7. The electronic sensory simulation system of claim 2, wherein the user interface allows the user to configure the system to be active for a predetermined length of time.

8. The electronic sensory simulation system of claim 1, wherein the sensory unit assembly is capable of being provided with pre-designed sensory combinations which include a pre-defined scent, a pre-defined visual component, and a pre-defined auditory component.

9. The electronic sensory simulation system of claim 1, wherein the user interface is able to receive input via a plurality of sources selected from the group consisting of an audio in jack, SD memory card, microSD memory card, USB, and HDMI.

10. The electronic sensory simulation system of claim 1, wherein the at least one scent diffusing mechanism accepts at least one selected from the group consisting of scent pods, scent cartridges, liquid refills, and essential oils.

11. The electronic sensory simulation system of claim 1, wherein the powerer includes a rechargeable battery and charging port.

12. A system comprising:
a sensory unit assembly, the sensory unit assembly including:
  a display screen;
  at least one speaker;
  at least one scent diffusing mechanism having a receptacle configured to receive a scent insert;
  a powerer;
  a user interface, the user interface having a plurality of buttons for configuring and operating the system, and input ports for receiving information; and
a docking station, the docking station including:
  a horizontal or vertical base;
  a docking port;
  a charging interface between the sensory unit assembly and the docking port; and
  a power supply;
wherein the user interface provides a user with control options to activate or deactivate the system, and make selections for configuring system functions;
  wherein the sensory unit assembly is capable of being provided with pre-designed sensory combinations which include a pre-defined scent, a pre-defined visual component, and a pre-defined auditory component;
  wherein the sensory unit assembly is capable of being configured with individual sensory choices selected by the user for scent, visual display, and audio;
  wherein the user interface allows the user to determine a brightness of the display screen;
  wherein the user interface allows the user to determine a volume of audio played via the at least one speaker;
  wherein the user interface allows the user to configure the system to be active for a predetermined length of time;
  wherein the sensory unit assembly includes an extendable support member which allows the sensory unit assembly to be supported in an upright position when on a generally planar horizontal surface;
  wherein the extendable support member is configured to be stored within the sensory unit assembly during a non-use condition; and
  wherein the powerer includes a rechargeable battery and charging port.

* * * * *